United States Patent [19]

Kajimoto et al.

[11] Patent Number: 4,900,820

[45] Date of Patent: * Feb. 13, 1990

[54] PROCESS FOR PRODUCING CYCLIC UREAS

[75] Inventors: Nobuyuki Kajimoto; Teruyuki Nagata; Masaru Wada, all of Fukuoka, Japan

[73] Assignee: Mitsui Toatsu Chemicals, Inc., Tokyo, Japan

[*] Notice: The portion of the term of this patent subsequent to Mar. 15, 2005 has been disclaimed.

[21] Appl. No.: 53,387

[22] Filed: May 22, 1987

[30] Foreign Application Priority Data

Jun. 12, 1986 [JP] Japan ............................. 61-134888
Jun. 12, 1986 [JP] Japan ............................. 61-148056

[51] Int. Cl.⁴ ................. C07D 233/34; C07D 239/10; C07D 243/04
[52] U.S. Cl. .................................... 540/492; 544/315; 548/317
[58] Field of Search ................ 548/317; 544/315; 540/402

[56] References Cited

U.S. PATENT DOCUMENTS 3,073,800 1/1963 Shiu Yim Poon ..................... 260/69
4,731,453 3/1988 Nagata et al. ....................... 548/317

FOREIGN PATENT DOCUMENTS 0198345 10/1986 European Pat. Off. .
1121617 1/1962 Fed. Rep. of Germany .
1445640 12/1968 Fed. Rep. of Germany .

OTHER PUBLICATIONS

Justus Liebigs Annalen der Chemie, vol. 726, 1969, pp. 89-99, Verlag Chemie GmbH, Weinheim, DE; H. Petersen: "Synthese und Eigenschaften Funfgliedriger cyclischer Harnstoffe", p. 93, cormulas 32-31; pp. 97, 31a, b.

Journal of Medicinal Chemistry, vol. 14, No. 2, Feb. 1971, pp. 138-144, et al: "Centrally Acting Cyclic Urea, Thiourea, and their N,N'dialkyl derivatives., Structure-Activity Correlations", Hussain et al.

Primary Examiner—John M. Ford
Attorney, Agent, or Firm—Albert L. Jeffers; John F. Hoffman; Lawrence A. Steward

[57] ABSTRACT

A process for producing a cyclic diamine which comprises reacting a diamine of the formula $$R-HN-R'-NH-R \qquad (II)$$

wherein R represents a lower alkyl group and R' represents a lower alkyl group-substituted dimethylene group, trimethylene group, a lower alkyl group-substituted trimethylene group, tetramethylene group or a lower alkyl group-substituted tetramethylene group with urea in the presence of a polar solvent and at 180° C. or higher, to obtain a cyclic urea

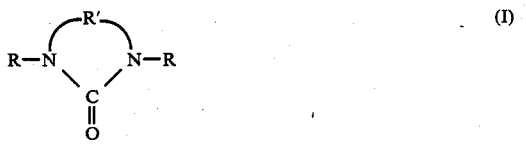

wherein R and R' are each as defined above, the production yield being more improved by carrying out the initial period reaction at 140° C. or lower.

6 Claims, No Drawings

PROCESS FOR PRODUCING CYCLIC UREAS

BACKGROUND OF THE INVENTION

1. Field of the Invention

This invention relates to a process for producing a cyclic urea expressed by the formula (I)

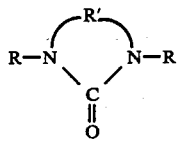
(I)

wherein R represents a lower alkyl group and R' represents a lower alkyl group-substituted dimethylene group, trimethylene group, a lower alkyl group-substituted trimethylene group, tetramethylene group or a lower alkyl group-substituted tetramethylene group, by reacting a diamine with urea.

Cyclic ureas of the formula (I) such as 2-imidazolidinones, tetrahydro-2(1H)-pyrimidinone, hexahydro-2H-1,3-diazepin-2-ones, etc. are useful substances as non-protonic polar solvents and as an intermediate for pharmaceuticals, pesticides, etc. Particularly the cyclic ureas are superior solvents for high molecular compounds such as polyamides, polyvinyl chloride, polyvinyl alcohol, polystyrene, polyurethanes, phenolic resins, etc. and also are easily soluble in many inorganic compounds and further are used as a solvent for various characteristic organic reactions.

2. Description of the Related Art

As to the process for production of the above-mentioned cyclic ureas using a diamine and urea, some processes have been proposed. For example, as to production of 1,3,4-trimethyl-2-imidazolidinone, there has been known a process of reacting N,N'-dimethyl-1,2-propanediamine with urea to obtain the objective product with a yield of 75% [Liebig, Ann. der Chem., vol. 726, page 97 (1969)]. However, this process uses an excess quantity of the diamine, that is, 1.5 mol per mol of urea in order to improve the operation of the reaction mass and the yield. Since such an excess diamine is expensive, it is necessary to recover it from the reaction mass. Further the yield of 75% is still unsatisfactory in the aspect of commercial production process.

Further, a process has been known wherein N,N'-diethyl-1,3-propanediamine or N,N'-dipropyl-1,3-propanediamine is reacted with urea to obtain 1,3-diethyltetrahydro-2(1H)-pyrimidinone or tetrahydro-1,3-dipropyl-2(1H)-pyrimidinone with a yield of 64.0% or 21.5%, respectively (J. Med. Chem., vol. 14, page 140 (1971)). These processes are also commercially unsatisfactory due to the low yields of the objective products.

SUMMARY OF THE INVENTION

The object of the present invention is to provide an improved process for reacting a diamine as described above directly with urea to produce a cyclic urea of the formula (I) with a high yield and at a commercially cheap cost.

The present invention resides in a process for producing a cyclic urea expressed by the formula (I)

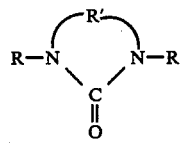
(I)

wherein R represents a lower alkyl group and R' represents a lower alkyl group-substituted dimethylene group, trimethylene group, a lower alkyl group-substituted trimethylene group, tetramethylene group or a lower alkyl group-substituted tetramethylene group, by reacting a diamine expressed by the formula (II)

$$R\text{—}HN\text{—}R'\text{—}NH\text{—}R \qquad (II)$$

wherein R and R' are each as defined above, with urea, which process comprises carrying out the reaction in the presence of a polar solvent and at a temperature of 180° C. or higher.

DETAILED DESCRIPTION OF PREFERRED EMBODIMENTS

The present inventors have made extensive research on a commercial process for producing a cyclic urea by reacting a diamine with urea, and as a result have obtained the following findings to thereby complete the present invention:

(1) When the reaction is carried out in the presence of a polar solvent and at a temperature of 180° C. or higher, it is possible to obtain a cyclic urea with a high yield.

Usually in the reaction of diamines with urea, urea intermediates of the diamines are formed before cyclic ureas are formed. In many cases, the intermediates have a low solubility in non-polar solvents so that they are deposited outside the system. However, unless the intermediates have a temperature of 180° C. or higher in the dissolved state thereof, the rate of the ring closure reaction thereof into cyclic ureas is very low.

For this reason, reaction of diamines with urea in a polar solvent having a high solubility and at a temperature of 180° C. or higher makes it possible to obtain cyclic ureas with a high yield.

(2) Further, in the reaction of diamines with urea in a polar solvent, the reaction is carried out at a temperature of 140° C. or lower until the urea intermediates of the diamines are formed, followed by carrying out the reaction at a temperature of 180° C. or higher, to further raise the yield.

In the reaction of diamines with urea in a polar solvent, the initial period reaction before formation of the urea intermediates do not particularly require a temperature of 180° C. or higher. The reaction rate is low at a temperature of 100° C. or lower, but it proceeds sufficiently at a temperature in the vicinity of 100° C. to that of 140° C. or lower. At a temperature of 180° C. or higher, urea itself is thermally decomposed, resulting in urea loss. Thus it has been found that in the case of the two-stage temperature elevation reaction process, urea is reacted without any waste.

The reaction end point of the urea intermediates of diamines can be easily judged from completion of ammonia evolution. According to the two-stage temperature elevation process, since diamines and urea are both used without any waste, it is unnecessary to use both diamines and urea particularly in excess, and the molar ratio of diamines/urea fed is preferably in the range of 0.6–1.2, more preferably nearly equimolar. If diamines are fed in excess, operation of recovering expensive diamines is to be added. Further if urea is fed in excess, solid impurities such as cyanuric acid as a thermal decomposition product of urea remain so that troublesome solid-liquid operation is to be added.

(3) Further, the present inventors have made extensive research on a commercial process and as a result have found the following invention:

When the above-mentioned two-stage temperature elevation process is employed, the initial period reaction at a temperature of 140° C. or lower raises no problem, but since the boiling points of diamines are 180° C. or less in many cases, if the temperature is raised to higher temperatures than 180° C. to carry out the latter stage reaction, unreacted diamines remain so that it is difficult to carry out the reaction at higher temperatures than 180° C. under the atmospheric pressure; hence it is necessary to carry out the reaction under pressure for example using an autoclave. In such a situation, the present inventors have found another preferred process. Namely, a diamine and urea are fed in the presence of a pair solvent at the beginning of the reaction so as to give a molar ratio of diamine/urea of about ½, followed by carrying out the reaction at a temperature of 140° C. or lower till formation of an urea intermediate at the initial period reaction is completed, and successively carrying out reaction at a temperature of 180° C. or higher while adding the diamine so as to give a molar ratio of the total diamine/urea of about 2/2 to obtain a cyclic urea with a high yield even at the atmospheric pressure.

The reason of success of this process is as follows:

Since urea in a quantity of about twice that of the diamine is fed at the beginning of the reaction and reacted, the urea intermediate formed at the initial period reaction is converted into a non-volatile diurea product of the diamine and no diamine as raw material remains so that temperature elevation up to 180° C. or higher is possible even at the atmospheric pressure. Thus according to this process, if the boiling point of the solvent is 180° C. or higher, it is possible to carry out the reaction even at the atmospheric pressure throughout the total reaction. Further, it has been found that the diamine added at 180° C. or higher is effectively used for the reaction and hence this process is not inferior also in the aspect of yield to the above process of carrying out reaction according to the two-stage temperature elevation process using two materials together.

As the solvent used in the process of the present invention, hydrocarbons and halogenated hydrocarbons are unsuitable and polar solvents are used. Examples of preferred solvents are non-protonic polar solvents such as N,N'-dimethylformamide, N,N'-dimethylacetamide, tetramethylurea, dimethylsulfoxide, hexamethylphosphoramide, sulfolane, methyl isobutyl ketone, nitrobenzene, tetrahydrofuran, dioxane, etc. Further, if the boiling point is low, since too a large pressure vessel is required, solvents having a boiling point of 180° C. or higher are preferred, and particularly in order to avoid the troublesomeness of solvent separation, it is particularly preferred to use the same cyclic ureas as those formed in the reaction of the present invention.

The lower alkyl group as R and R' in the formula (II) is preferably methyl, ethyl, propyl, butyl, etc.

Concrete examples of diamines of the formula (II) wherein R represents a lower alkyl group and R' represents a lower alkyl-substituted dimethylene group (those obtained by replacing at least one hydrogen atom of dimethylene group by a lower alkyl group) are N,N'-dimethyl-1,2-propanediamine, N,N'-2-trimethyl-2,3-butanediamine, N,N'-diethyl-1,2-propanediamine, etc.

Further, concrete examples of diamines of the formula (II) wherein R represents a lower alkyl group and R' represents trimethylene group, a lower alkyl group-substituted trimethylene group (those obtained by replacing at least one hydrogen atom of trimethylene group by a lower alkyl group), tetramethylene group or a lower alkyl group-substituted tetramethylene group (those obtained by replacing at least one hydrogen atom of tetramethylene group by a lower alkyl group) are N,N'-dimethyl-1,3-propanediamine, N,N'-diethyl-1,3-propanediamine, N,N'-dipropyl-1,3-propanediamine, N,N'-dibutyl-1,3-propanediamine, N,N',2-trimethyl-1,3-propanediamine, N,N',2,2-tetramethyl-1,3-propanediamine; N,N'-dimethyl-1,4-butanediamine, N,N'-diethyl-1,4-butanediamine, N,N'-dipropyl-1,4-butanediamine, N,N'-dibutyl-1,4-butanediamine, etc.

The cyclic ureas expressed by the formula (I) obtained according to the present invention are the corresponding cyclic ureas obtained by using the above-mentioned diamines. Examples thereof are 1,3,4-trimethyl-2-imidazolidinone, 1,3,4,4,5-pentamethyl-2-imidazolidinone, 1,3-diethyl-4-methyl-2-imidazolidinone, tetrahydro-1,3-dimethyl-2(1H)-pyramidinone, 1,3-diethyltetrahydro-2(1H)-pyrimidinone, tetrahydro-1,3-dipropyl-2(1H)-pyrimidinone, 1,3-dibutyltetrahydro-2(1H)-pyrimidinone, tetrahydro-1,3,5-trimethyl-2(1H)-pyrimidinone, tetrahydro-1,3,5,5-tetramethyl-2(1H)-pyrimidinone; hexahydro-1,3-dimethyl-2H-1,3-diazepin-2-one, 1,3-diethylhexahydro-2H-1,3-diazepin-2-one, hexahydro-1,3-dipropyl-2H-1,3-diazepin-2-one, 1,3-dibutylhexahydro-2H-1,3-diazepin-2-one, etc.

Next a preferred usual embodiment of the process of the present invention will be described.

In the case of the reaction under pressure, a diamine and urea as the raw materials and a polar solvent are fed into an autoclave equipped with a thermometer and a mechanical stirrer, followed by raising the temperature to 180° C. or higher and reacting these materials. The upper limit of the temperature has no particular limitation, but if it exceeds 300° C., a problem is raised in the aspect of heating method and energy cost.

Further, in the case where the reaction is carried out according to the two-stage temperature elevation process, reaction is carried out at a temperature of 140° C. or lower at the initial period of the reaction till formation of the urea intermediate of the diamine is completed, followed by raising the temperature to 180° C. or higher and reacting the reaction mixture.

Further, according to the process wherein the diamine is added at the time of the latter stage reaction, a diamine, urea and a polar solvent are fed into a reactor equipped with a reflux condenser, a thermometer, a dropping funnel and a mechanical stirrer and reacted at a temperature of 140° C. or lower till ammonia evolution is completed, followed by raising the temperature to 180° C. or higher and reacting the reaction mixture while adding the diamine through the dropping funnel. After completion of the reaction, it is possible to take out the resulting cyclic urea by way of distillation or the like. Particularly when the same cyclic urea as that formed by the reaction is used as the solvent for the reaction, separation of the product from the solvent is unnecessary; hence the process is a very simplified one.

According to the process for producing cyclic ureas by reacting diamines with urea of the present invention, the objective product is obtained with a high yield without using expensive diamines in excess as compared with conventional processes, and also the operation is superior.

Particularly when the reaction is carried out with a two-stage temperature gradient, the yield is more improved, and moveover when diamines are fed in a quantity of about ½ mol per mol of urea at the initial period of the reaction and the latter stage reaction is carried out under cumulative addition of the diamines so as to give an equivalent mol in total, it is possible to carry out the whole reaction under the atmospheric pressure.

The present invention will be described in more detail by way of Examples.

EXAMPLE 1

Into a 500 ml stainless autoclave were fed N,N'-dimethyl-1,2-propanediamine (102.2 g, 1.00 mol), urea (60.1 g, 1.00 mol) and 1,3,4-trimethyl-2-imidazolidinone (100 g), followed by raising the temperature up to a reaction temperature of 210° C. over about 30 minutes and reacting these materials at this temperature for 3 hours.

After completion of the reaction, the quantity of 1,3,4-trimethyl-2-imidazolidinone was determined according to gas chromatography. The production yield was 85.3%. The reaction mass was distilled under reduced pressure to obtain 1,3,4-trimethyl-2-imidazolidinone (a fraction of b.p. 133°–135° C./20 torr) (202.6 g).

EXAMPLE 2

Reaction was carried out in the same manner as in Example 1 except that the raw material N,N'-dimethyl-1,2-propanediamine was replaced by N,N',2-trimethyl-2,3-butanediamine (130.3 g, 1.00 mol) and 1,3,4-trimethyl-2-imidazolidinone as the solvent was replaced by 1,3,4,4,5-pentamethyl-2-imidazolidinone (100 g), followed by analysis. As a result, the production yield of 1,3,4,4,5-pentamethyl-2-imidazolidinone was 84.7%.

EXAMPLE 3

Reaction was carried out in the same manner as in Example 1 except that the raw material N,N'-dimethyl-1,2-propanediamine was replaced by N,N'-diethyl-1,2-propanediamine (130.3 g, 1.00 mol) and 1,3,4-trimethyl-2-imidazolidinone as the solvent was replaced by 1,3-diethyl-4-methyl-2-imidazolidinone (100 g), followed by analysis. As a result, the production yield of 1,3-diethyl-4-methyl-2-imidazolidinone was 83.3%.

EXAMPLES 4–10

Reactions were carried out in the same manner as in Example 1 except that 1,3,4-trimethyl-2-imidazolidinone as the solvent was replaced by various solvents (100 g) listed in Table 1, followed by analysis. The production yields with the respective solvents are shown in Table 1.

TABLE 1

| Example No. | Solvent | Production yield (%) |
|---|---|---|
| 4 | Toluene | 6.1 |
| 5 | 1,2-Dichloroethane | 23.7 |
| 6 | Ethylene glycol | 60.3 |
| 7 | Isopropyl alcohol | 71.9 |
| 8 | Methyl isobutyl ketone | 83.5 |
| 9 | N—methyl-2-pyrrolidone | 86.1 |

TABLE 1-continued

| Example No. | Solvent | Production yield (%) |
|---|---|---|
| 10 | N,N—dimethylacetamide | 82.8 |

EXAMPLE 11

Into a 500 ml stainless autoclave were fed N,N'-dimethyl-1,2-propanediamine (102.2 g, 1.00 mol), urea (60.1 g, 1.00 mol) and 1,3,4-trimethyl-2-imidazolidinone (100 g), followed by raising the temperature and reacting these materials at a reaction temperature of 120° C. for 8 hours and successively raising the temperature up to 210° C. to react the reaction mixture for 3 hours.

After completion of the reaction, the quantity of 1,3,4-trimethyl-2-imidazolidinone was determined according to gas chromatography. The production yield of 1,3,4-trimethyl-2-imidazolidinone was 94.9%.

EXAMPLE 12

Reaction was carried out in the same manner as in Example 11 except that the raw material N,N'-dimethyl-1,2-propanediamine was replaced by N,N',2-trimethyl-2,3-butanediamine (130.3 g, 1.00 mol) and 1,3,4-trimethyl-2-imidazolidinone as the solvent was replaced by 1,3,4,4,5-pentamethyl-2-imidazolidinone (100 g), followed by analysis. As a result, the production yield of 1,3,4,4,5-pentamethyl-2-imidazolidinone was 93.3%.

EXAMPLES 13–16

Reaction was carried out in the same manner as in Example 11 except that 1,3,4-trimethyl-2-imidazolidinone as the solvent was replaced by various solvents (100 g) listed in Table 2, followed by analysis. The production yields of 1,3,4-trimethyl-2-imidazolidinone with the respective solvents are shown in Table 2.

TABLE 2

| Example No. | Solvent | Production yield (%) |
|---|---|---|
| 13 | Toluene | 7.8 |
| 14 | 1,2-Dichloroethane | 26.4 |
| 15 | N—methyl-2-pyrrolidone | 94.6 |
| 16 | N,N—dimethylacetamide | 95.2 |

EXAMPLE 17

Into a 300 ml glass flask equipped with a reflux condenser, a thermometer, a dropping funnel and a stirrer were fed N,N'-dimethyl-1,2-propanediamine (51.1 g, 0.50 mol, urea (60.1 g, 1.00 mol) and 1,3,4-trimethyl-2-imidazolidinone (100 g), and N,N'-dimethyl-1,2-propanediamine (51.1 g, 0.50 mol) was fed into the dropping funnel. The temperature was raised to 120° C. and the above materials were reacted. As the reaction advanced, NH3 gas evolved and the evolution of NH3 gas ceased after about 2 hours. Successively the temperature was raised to 210° C. After the temperature reached about 200° C., N,N'-dimethyl-1,2-propanediamine was dropwise added through the dropping funnel over about 2 hours, followed by reacting the reaction mixture at the same temperature for one hour.

After completion of the reaction, the quantity of 1,3,4-trimethyl-2-imidazolidinone was determined. As a result, its production yield was 96.2%. The reaction mass was distilled under reduced pressure to obtain 1,3,4-trimethyl-2-imidazolidinone (a fraction of b.p. 133 -135° C./20 torr) (215.4 g).

EXAMPLE 18

Reaction was carried out in the same manner as in Example 17 except that N,N'2-trimethyl-2,3-butanediamine (65.1 g, 0.50 mol) in place of the raw material N,N'-dimethyl-1,2-propanediamine was fed into the reaction flask and also N,N',2-trimethyl-2,3-butanediamine (65.1 g, 0.50 mol) was fed into the dropping funnel, and the solvent 1,3,4-trimethyl-2-imidazolidinone was replaced by 1,3,4,4,5-pentamethyl-2-imidazolidinone (100 g), followed by analysis. As a result, the production yield of 1,3,4,4,5-pentamethyl-2-imidazolidinone was 95.4%.

EXAMPLE 19

Reaction was carried out in the same manner as in Example 17 except that N,N'-diethyl-1,2-propanediamine (65.1 g, 0.50 mol) in place of the raw material N,N'-dimethyl-1,2-propanediamine was fed into the reaction flask and N,N'-diethyl-1,2-propanediamine (65.1 g, 0.50 mol) was fed into the dropping funnel, and further 1,3-diethyl-4-methyl-2-imidazolidinone (100 g) in place of 1,3,4-trimethyl-2-imidazolidinone as the solvent was fed, followed by analysis. As a result, the production yield was 93.5%.

EXAMPLES 20-24

Reactions were carried out in the same manner as in Example 17 except that the solvent 1,3,4-trimethyl-2-imidazolidinone was replaced by various solvents (100 g) listed in Table 3, followed by analysis. The production yields with the respective solvents are shown in Table 3.

TABLE 3

| Example No. | Solvent | Production yield (%) |
|---|---|---|
| 20 | Tetralin | 4.3 |
| 21 | 1-Chloronaphthalene | 13.2 |
| 22 | Diethylene glycol | 52.9 |
| 23 | Hexamethylphosphoramide | 96.0 |
| 24 | Sulfolane | 93.9 |

EXAMPLE 25

Into a 500 ml stainless autoclave were fed N,N'-dimethyl-1,3-propanediamine (102.2 g, 1.00 mol), urea (60.1 g, 1.00 mol) and tetrahydro-1,3-dimethyl-2(1H)-pyrimidinone (100 g).

The temperature was raised to a reaction temperature of 210° C. over about 30 minutes and the above materials were reacted at the same temperature (210° C.) for 3 hours.

After completion of the reaction, the quantity of tetrahydro-1,3-dimethyl-2(1H)-pyrimidinone was determined according to gas chromatography. The production yield was 86.1%. The reaction mass was distilled under reduced pressure to obtain tetrahydro-1,3-dimethyl-2(1H)-pyrimidinone (a fraction of b.p. 93°-94° C./5 torr) (203.5 g).

EXAMPLES 26-37

Reactions were carried out in the same manner as in Example 25 except that the raw material diamine and the solvent were respectively varied, followed by determining the quantities of the resulting products according to gas chromatography. Used diamines and solvents and the resulting products and production yields are shown in Table 4.

EXAMPLE 38

Into a 500 ml stainless autoclave were fed N,N'-dimethyl-1,3-propanediamine (102.2 g, 1.00 mol), urea (60.1 g, 1.00 mol) and tetrahydro-1,3-dimethyl-2(1H)-pyrimidinone (100 g), followed by raising the temperature, reacting these materials at a reaction temperature of 120° C. for 8 hours, successively raising the temperature to 210° C. and further reacting the reaction mixture for 3 hours.

After completion of the reaction, the quantity of tetrahydro-1,3-dimethyl-2(1H)-pyrimidinone was determined. The production yield of tetrahydro-1,3-dimethyl-2(1H)-pyrimidinone was 96.3%.

EXAMPLES 39-44

Reactions were carried out in the same manner as in Example 38 except that the raw material diamine and the solvent were respectively varied, followed by determining the quantities of the products according to gas chromatography. The used raw material diamines and solvents and the resulting products and production yields are shown in Table 4.

EXAMPLE 45

Into a 500 ml glass flask equipped with a reflux condenser, a thermometer, a dropping funnel and a stirrer were fed N,N'-dimethyl-1,3-propanediamine (51.1 g, 0.50 mol), urea (60.1 g, 1.00 mol) and tetrahydro-1,3-dimethyl-2(1H)-pyrimidinone (100 g), and N,N'-dimethyl-1,3-propanediamine (51.1 g, 0.50 mol) was fed into the dropping funnel. The temperature was raised to 120° C. and the above materials were reacted. As the reaction advanced, NH$_3$ gas evolved, and after 2 hours, evolution of NH$_3$ gas ceased. Successively the temperature was raised to 210° C. After the reaction reached about 200° C., N,N'-dimethyl-1,3-propanediamine was dropwise added through the dropping funnel over about 2 hours, followed by reacting the reaction mixture at 210° C. for one hour. The reaction mass after completion of the reaction was subjected to determination of the quantity of tetrahydro-1,3-dimethyl-2(1H)-pyrimidinone according to gas chromatography. As a result, the production yield was 96.0%. The reaction mass was distilled under reduced pressure to obtain tetrahydro-1,3-dimethyl-2(1H)-pyrimidinone (a fraction of b.p. 93°-94° C./5 torr) (215.0 g).

EXAMPLES 46-55

Reactions were carried out in the same manner as in Example 45 except that the raw material diamine and solvent were respectively varied, followed by determining the quantities of the products according to gas chromatography. The used raw material diamines and solvents and the resulting products and production yields are shown in Table 4.

TABLE 4

| Example No. | Raw material diamine Name | Weight (g) of feed | Mol of feed | Solvent Name | Weight (g) of feed | Cyclic urea produced Name | Production yield |
|---|---|---|---|---|---|---|---|
| 25 | N,N'—dimethyl-1,3-propanediamine | 102.2 | 1.00 | Tetrahydro-1,3-dimethyl-2(1H)—pyrimidione | 100 | Same as solvent | 86.1 |
| 26 | N,N'—diethyl-1,3-propanediamine | 130.3 | 1.00 | 1,3-diethyltetrahydro-2(1H)—pyrimidinone | 100 | Same as solvent | 85.2 |
| 27 | N,N—dipropyl-1,3-propanediamine | 158.3 | 1.00 | Tetrahydro-1,3-dipropyl-2(1H)—pyrimidinone | 100 | Same as solvent | 84.7 |
| 28 | N,N',2,2-tetramethyl-1,3-propanediamine | 130.3 | 1.00 | Tetrahydro-1,3,5,5-tetramethyl-2(1H)-pyrimidinone | 100 | Same as solvent | 85.5 |
| 29 | N,N'—dimethyl-1,4-butanediamine | 116.2 | 1.00 | Hexahydro-1,3-dimethyl-2H—1,3-diazepin-2-one | 100 | Same as solvent | 82.5 |
| 30 | N,N'—dipropyl-1,4-butanediamine | 172.4 | 1.00 | Hexahydro-1,3-dipropyl-2H—1,3-diazepin-2-one | 100 | Same as solvent | 83.9 |
| 31 | N,N'—dimethyl-1,3-propanediamine | 102.2 | 1.00 | Toluene | 100 | Tetrahydro-1,3-dimethyl-2(1H)—pyrimidinone | 4.9 |
| 32 | N,N'—dimethyl-1,3-propanediamine | 102.2 | 1.00 | 1,2-Dichloroethane | 100 | Tetrahydro-1,3-dimethyl-2(1H)—pyrimidinone | 21.4 |
| 33 | N,N'—dimethyl-1,3-propanediamine | 102.2 | 1.00 | Ethylene glycol | 100 | Tetrahydro-1,3-dimethyl-2(1H)—pyrimidinone | 62.7 |
| 34 | N,N'—dimethyl-1,3-propanediamine | 102.2 | 1.00 | Isopropyl alcohol | 100 | Tetrahydro-1,3-dimethyl-2(1H)—pyrimidinone | 70.3 |
| 35 | N,N'—dimethyl-1,3-propanediamine | 102.2 | 1.00 | Methyl isobutyl ketone | 100 | Tetrahydro-1,3-dimethyl-2(1H)—pyrimidinone | 82.8 |
| 36 | N,N'—dimethyl-1,3-propanediamine | 102.2 | 1.00 | N—methyl-2-pyrrolidone | 100 | Tetrahydro-1,3-dimethyl-2(1H)—pyrimidinone | 85.0 |
| 37 | N,N'—diemthyl-1,3-propanediamine | 102.2 | 1.00 | N,N'—dimethylacetamide | 100 | Tetrahydro-1,3-dimethyl-2(1H)—pyrimidinone | 84.2 |
| 38 | N,N'—dimethyl-1,3-propanediamine | 102.2 | 1.00 | Tetrahydro-1,3-dimethyl-2(1H)—pyrimidinone | 100 | Same as solvent | 96.3 |
| 39 | N,N',2,2-tetramethyl-1,3-propanediamine | 130.3 | 1.00 | Tetrahydro-1,3,5,5-tetramethyl-2(1H)—pyrimidinone | 100 | Same as solvent | 96.3 |
| 40 | N,N'—diethyl-1,4-butanediamine | 144.3 | 1.00 | 1,3-Diethylhexahydro-2H—1,3-diazepin-2-one | 100 | Same as solvent | 92.7 |
| 41 | N,N'—dimethyl-1,3-propanediamine | 102.2 | 1.00 | Toluene | 100 | Tetrahydro-1,3-dimethyl-2(1H)—pyrimidinone | 6.1 |
| 42 | N,N'—dimethyl-1,3-propanediamine | 102.2 | 1.00 | 1,2-Dichloroethane | 100 | Tetrahydro-1,3-dimethyl-2(1H)—pyrimidinone | 23.9 |
| 43 | N,N'—dimethyl-1,3-propanediamine | 102.2 | 1.00 | N—methyl-2-pyrrolidone | 100 | Tetrahydro-1,3-dimethyl-2(1H)—pyrimidinone | 94.5 |
| 44 | N,N'—dimethyl-1,3-propanediamine | 102.2 | 1.00 | N,N'—dimethylacetamide | 100 | Tetrahydro-1,3-dimethyl-2(1H)—pyrimidinone | 93.4 |
| 45 | N,N'—dimethyl-1,3-propanediamine | 51.1 + additional 51.1 | 0.50 + additional 0.50 | Tetrahydro-1,3-dimethyl-2(1H)—pyrimidinone | 100 | Same as solvent | 96.0 |
| 46 | N,N'—diethyl-1,3-propanediamine | 65.1 + additional 65.1 | 0.50 + additional 0.50 | 1,3-diethyltetrahydro-2(1H)—pyrimidinone | 100 | Same as solvent | 94.7 |
| 47 | N,N'—dipropyl-1,3-propanediamine | 79.2 + additional 79.2 | 0.50 + additional 0.50 | Tetrahydro-1,3-dipropyl 2(1H)—pyrimidinone | 100 | Same as solvent | 93.9 |
| 48 | N,N',2,2-tetramethyl-1,3-propanediamine | 65.1 + additional 65.1 | 0.50 + additional 0.50 | Tetrahydro-1,3,5,5-tetramethyl-2(1H)—pyrimidinone | 100 | Same as solvent | 95.2 |
| 49 | N,N'—dimethyl-1,4-butanediamine | 58.1 + additional 58.1 | 0.50 + additional 0.50 | Hexahydro-1,3-dimethyl-2H—1,3-diazepin-2-one | 100 | Same as solvent | 91.1 |
| 50 | N,N'—dipropyl-1,4-butanediamine | 86.2 + additional 86.2 | 0.50 + additional 0.50 | Hexahydro-1,3-dipropyl-2H—1,3-diazepin-2-one | 100 | Same as solvent | 91.3 |
| 51 | N,N'—dimethyl-1,3-propanediamine | 51.1 + additional 51.1 | 0.50 + additional 0.50 | Tetralin | 100 | Tetrahydro-1,3-dimethyl-2(1H)—pyrimidinone | 8.3 |
| 52 | N,N'—dimethyl-1,3-propanediamine | 51.1 + additional 51.1 | 0.50 + additional 0.50 | 1-Chloronaphthalene | 100 | Tetrahydro-1,3-dimethyl-2(1H)—pyrimidinone | 19.9 |
| 53 | N,N'—dimethyl-1,3-propanediamine | 51.1 + additional 51.1 | 0.50 + additional 0.50 | Diethylene glycol | 100 | Tetrahydro-1,3-dimethyl-2(1H)—pyrimidinone | 55.4 |
| 54 | N,N'—dimethyl-1,3- | 51.1 + | 0.50 + | Hexamethylphosphoro- | 100 | Tetrahydro-1,3-dimethyl- | 94.7 |

TABLE 4-continued

| Example No. | Raw material diamine Name | Weight (g) of feed | Mol of feed | Solvent Name | Weight (g) of feed | Cyclic urea produced Name | Production yield |
|---|---|---|---|---|---|---|---|
| | propanediamine | additional 51.1 | additional 0.50 | amide | | 2(1H)—pyrimidinone | |
| 55 | N,N'—dimethyl-1,3-propanediamine | 51.1 + additional 51.1 | 0.50 + additional 0.50 | Sulfolane | 100 | Tetrahydro-1,3-dimethyl-2(1H)—pyrimidinone | 95.1 |

What we claim is:

1. In a process for producing a cyclic urea expressed by the formula (I)

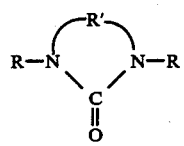  (I)

wherein R represents a lower alkyl group and R' represents a lower alkyl group-substituted dimethylene group, trimethylene group, a lower alkyl group-substituted trimethylene group, tetramethylene group or a lower alkyl group-substituted tetramethylene group, by reacting a diamine expressed by the formula (II)

R—HN—R'—NH—R  (II)

wherein R and R' are each defined above, with urea, the improvement comprising carrying out the reaction in the ratio of diamine to urea of about equimole in the presence of a non-protonic polar solvent and at a temperature of 180° C. or higher.

2. A process according to claim 1 wherein the reaction is carried out in a molar ratio of said diamine to urea of 0.6 to 1.2 in the presence of a polar solvent, first at a temperature of 140° C. or lower till formation of an urea intermediate with said diamine at the initial period reaction is completed, followed by successively raising the temperature to 180° C. or higher and further reacting the reaction mixture.

3. A process according to claim 1 wherein said diamine and urea are fed into a reactor in a molar ratio of said diamine to urea of about ½ in the presence of a polar solvent, first at a temperature of 140° C. or lower till formation of an urea intermediate with said diamine is completed, followed by successively raising the temperature to 180° C. or higher and further reacting the reaction mixture while adding said diamine so as to give a molar ratio of the total of said diamine to urea of about 2/2.

4. A process according to claim 1 wherein a cyclic urea expressed by the formula (I)

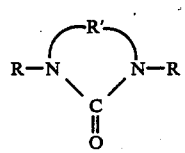  (I)

wherein R and R' are each as defined above, which is the same as the objective reaction product, is used as said polar solvent.

5. A process according to claim 2 wherein a cyclic urea expressed by the formula (I)

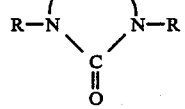  (I)

wherein R and R' are each as defined above, which is the same as the objective reaction product, is used as said polar solvent.

6. A process according to claim 3 wherein a cyclic urea expressed by the formula (I)

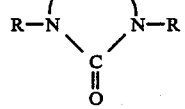  (I)

wherein R and R' are each as defined above, which is the same as the objective reaction product, is used as said polar solvent.

* * * * *